(12) United States Patent
Tamura

(10) Patent No.: US 8,951,198 B2
(45) Date of Patent: Feb. 10, 2015

(54) METHODS AND APPARATUS FOR ULTRASOUND IMAGING

(75) Inventor: Tadashi Tamura, North Haven, CT (US)

(73) Assignee: Hitachi Aloka Medical, Ltd., Tokyo (JP)

(*) Notice: Subject to any disclaimer, the term of this patent is extended or adjusted under 35 U.S.C. 154(b) by 0 days.

(21) Appl. No.: 13/608,453

(22) Filed: Sep. 10, 2012

(65) Prior Publication Data

US 2013/0261453 A1    Oct. 3, 2013

Related U.S. Application Data

(60) Provisional application No. 61/617,848, filed on Mar. 30, 2012.

(51) Int. Cl.
*A61B 8/00* (2006.01)

(52) U.S. Cl.
USPC .......................................... 600/438

(58) Field of Classification Search
USPC .......................................... 600/438
See application file for complete search history.

(56) References Cited

U.S. PATENT DOCUMENTS

| | | | |
|---|---|---|---|
| 5,606,971 | A | 3/1997 | Sarvazyan |
| 5,810,731 | A | 9/1998 | Sarvazyan et al. |
| 7,223,241 | B2 | 5/2007 | Radulescu |
| 7,252,004 | B2 | 8/2007 | Fink et al. |
| 8,197,408 | B2 | 6/2012 | Fan et al. |
| 2008/0188744 | A1* | 8/2008 | Fan et al. ............ 600/438 |
| 2009/0005682 | A1* | 1/2009 | Fan et al. ............ 600/443 |
| 2009/0257621 | A1* | 10/2009 | Silver ................. 382/103 |
| 2010/0286516 | A1* | 11/2010 | Fan et al. ............ 600/438 |
| 2012/0123263 | A1 | 5/2012 | Osaka et al. |

FOREIGN PATENT DOCUMENTS

| | | |
|---|---|---|
| WO | 2011/004661 A1 | 1/2011 |
| WO | 2011/126727 A2 | 10/2011 |

OTHER PUBLICATIONS

Maurice RL, Fromageau J, Brusseau E, Finet G, Rioufol G, Cloutier G, "On the Potential of the Lagrangian Estimator for Endovascular Ultrasound Elastography: in Vivo Human Coronary Artery Study", 2007, Ultrasound in Med. & Biol., vol. 33, No. 8, pp. 1199-1205, 2007.*

(Continued)

*Primary Examiner* — Tse Chen
*Assistant Examiner* — Lisa Kinnard
(74) *Attorney, Agent, or Firm* — Buckley, Maschoff & Talwalkar LLC

(57) ABSTRACT

A first ultrasound pulse is applied to biological tissue to create shear waves in the biological tissue, a focused ultrasound pulse is transmitted into the biological tissue, one or more ultrasound signals is received from the biological tissue, and shear waves are detected in the biological tissue based on the received one or more ultrasound signals. At least one propagation property associated with the detected shear waves is determined, and the determined at least one propagation property is displayed. A strain image is obtained by either acoustic radiation forces or mechanical compression, e.g., by an ultrasound probe. The strain image is then converted to a new shear wave velocity image by using a previously-obtained shear wave velocity image.

21 Claims, 17 Drawing Sheets

(56) References Cited

OTHER PUBLICATIONS

Maurice RL, Fromageau J, Brusseau E, Finet G, Rioufol G, Cloutier G, "On the Potential of the Lagrangian Estimator for Endovascular Ultrasound Elastography: in Vivo Human Coronary Artery Study", 2007, Ultrasound in Med. & Biol., vol. 33, No. 8, pp. 1199-1205.*

Patent Cooperation Treaty, "PCT International Search Report and PCT Written Opinion of the International Searching Authority", May 14, 2013, for International Application No. PCT/JP2013/059803, 6pgs.

* cited by examiner

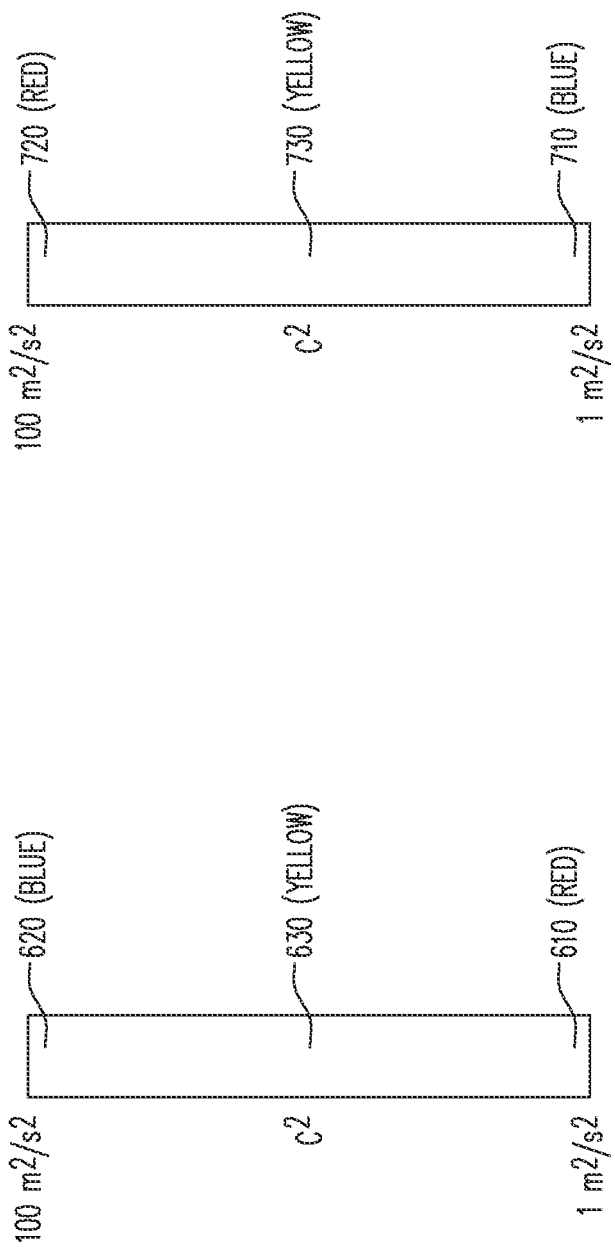

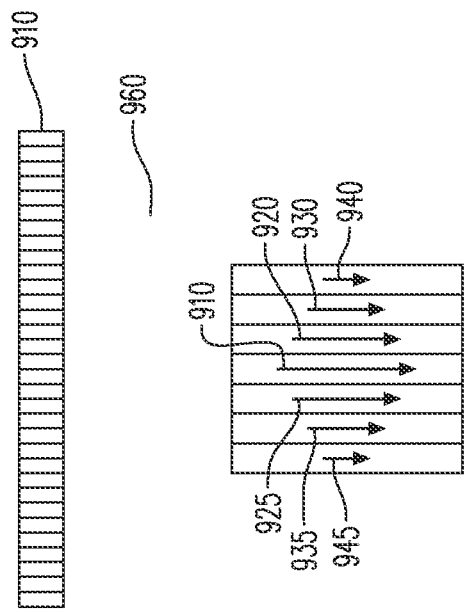
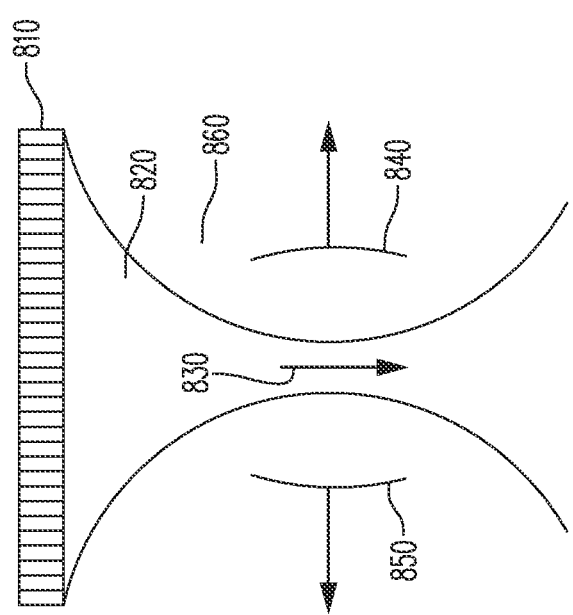

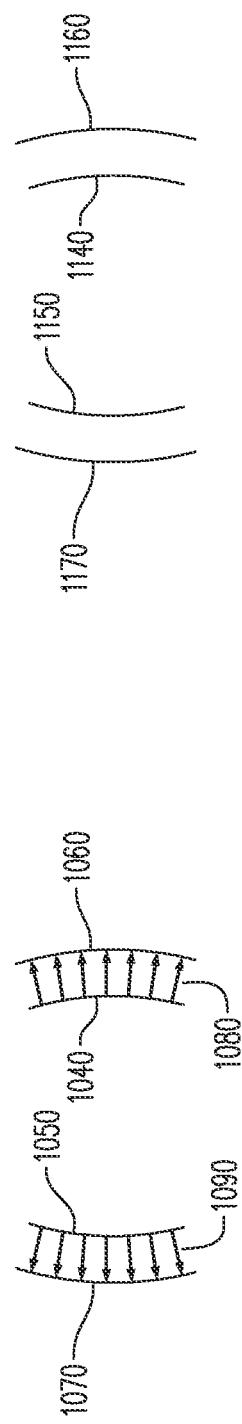
Figure 11
Figure 10

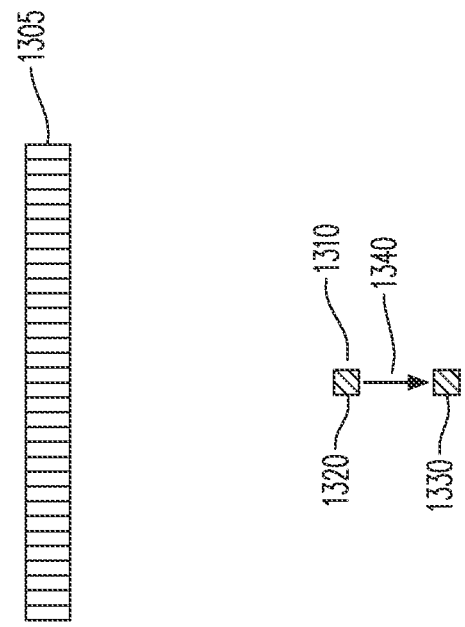
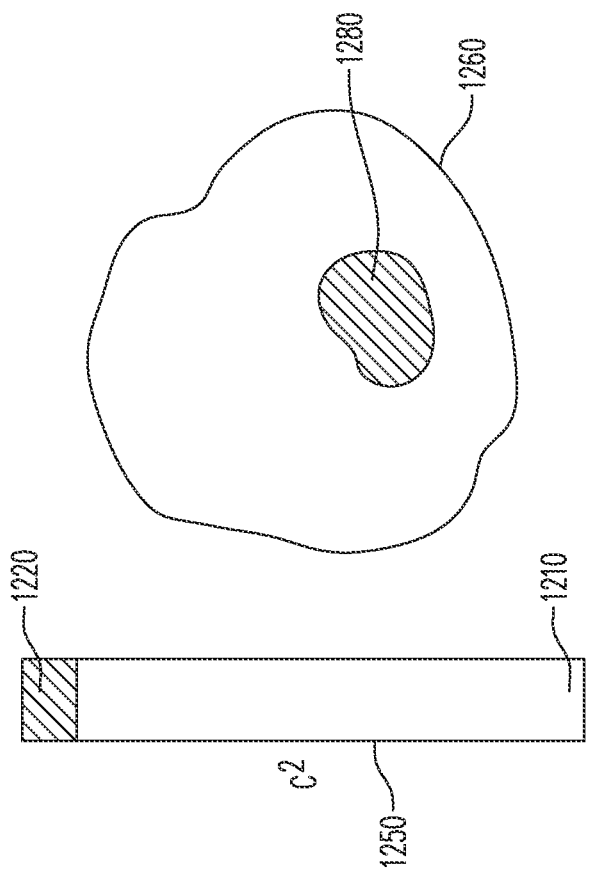

METHODS AND APPARATUS FOR ULTRASOUND IMAGING

CROSS-REFERENCE TO RELATED APPLICATIONS

The present application claims priority to U.S. Provisional Patent Application Ser. No. 61/617,848, filed on Mar. 30, 2012 and entitled "Method and Apparatus for Ultrasound Imaging", the contents of which are incorporated herein by reference for all purposes.

BACKGROUND

Systems and methods described herein generally relate to the field of ultrasound imaging. More specifically, embodiments described below relate to methods and systems for measuring shear wave velocity in tissue.

Pathological conditions may result in soft tissue which is stiffer than would be present under physiological conditions. Physicians therefore use palpation to locate stiff tissue within a body and thereby identify pathological conditions. For example, breast cancers are known to be generally harder than healthy breast tissue and may be detected as a hard lump through palpation.

The propagation velocity of shear waves in tissue is related to the stiffness (Young's modulus) of tissue by the following equation, $$E = 3\rho \cdot c^2 \qquad (1)$$

where c is the propagation velocity of shear wave, E is Young's modulus, and $\rho$ is the tissue density. Therefore, cancers or other pathological conditions may be detected in tissue by measuring the propagation velocity of shear waves passing through the tissue.

A shear wave may be created within tissue by applying a strong ultrasound pulse to the tissue. The ultrasound pulse may exhibit a high amplitude and a long duration (e.g., on the order of 100 microseconds). The ultrasound pulse generates an acoustic radiation force which pushes the tissue, thereby causing layers of tissue to slide along the direction of the ultrasound pulse. These sliding (shear) movements of tissue may be considered shear waves, which are of low frequencies (e.g., from 10 to 500 Hz) and may propagate in a direction perpendicular to the direction of the ultrasound pulse. The ultrasound pulse may propagate at a speed of 1540 m/s in tissue. However, the shear wave propagates much more slowly in tissue, approximately on the order of 1-10 m/s.

Since the tissue motion is generally in the axial direction (i.e., the ultrasound pulse direction) the shear waves may be detected using conventional ultrasound Doppler techniques. In this regard, the ultrasound Doppler technique is best suited to detect velocity in the axial direction. Alternately, shear waves may be detected by measuring a tissue displacement caused by the acoustic radiation force.

In order to accurately measure the propagation velocity of the shear wave, the shear wave needs to be tracked at a fast rate or a fast frame rate of several thousands frames per second. An image in a frame may consist of a few hundred ultrasound lines. A typical frame rate of regular ultrasound imaging is about 50 frames/s, which is too slow to track the shear wave propagation. Therefore, there exists a need to increase the frame rate while maintaining a good signal to noise ratio and good spatial resolution. Also, there exists a need to efficiently provide an indication of tissue stiffness.

Shear wave velocity imaging may exhibit limited spatial resolution. Lateral spatial resolution may be particularly limited because the measurement of shear wave velocity requires detection of shear wave at at least two lateral positions (i.e., at the positions of at least two ultrasound beams). On the other hand, tissue strain may be detected at using only one ultrasound beam. Therefore, tissue strain imaging may exhibit higher spatial resolution than shear wave velocity imaging. However, tissue strain imaging may yield only a qualitative measurement of tissue stiffness while shear wave velocity imaging provides a quantitative measure.

BRIEF DESCRIPTION OF THE DRAWINGS

FIG. 6. Color coding of shear wave propagation velocity squared.

FIG. 7. Color coding of shear wave propagation velocity squared.

FIG. 8. A diagram illustrating generation of shear waves by acoustic radiation forces and the propagation of shear waves.

FIG. 9. A diagram illustrating sliding movements of shear waves.

FIG. 10. A diagram illustrating the propagation of shear waves.

FIG. 11. A diagram illustrating the propagation of shear waves.

FIG. 12. An example of a color-coded image of shear wave propagation velocity squared in tissue.

FIG. 13. A diagram to illustrate tissue displacement caused by an acoustic radiation force.

DETAILED DESCRIPTION

Embodiments will be described with reference to the accompanying drawing figures wherein like numbers represent like elements throughout. Before embodiments of the invention are explained in detail, it is to be understood that embodiments are not limited in their application to the details of the examples set forth in the following description or illustrated in the figures. Other embodiments may be practiced or carried out in a variety of applications and in various ways. Also, it is to be understood that the phraseology and terminology used herein is for the purpose of description and should not be regarded as limiting. The use of "including," "comprising," or "having," and variations thereof herein is meant to encompass the items listed thereafter and equivalents thereof as well as additional items. The terms "mounted," "connected," and "coupled," are used broadly and encompass both direct and indirect mounting, connecting, and coupling. Further, "connected," and "coupled" are not restricted to physical or mechanical connections or couplings.

Figure 1:
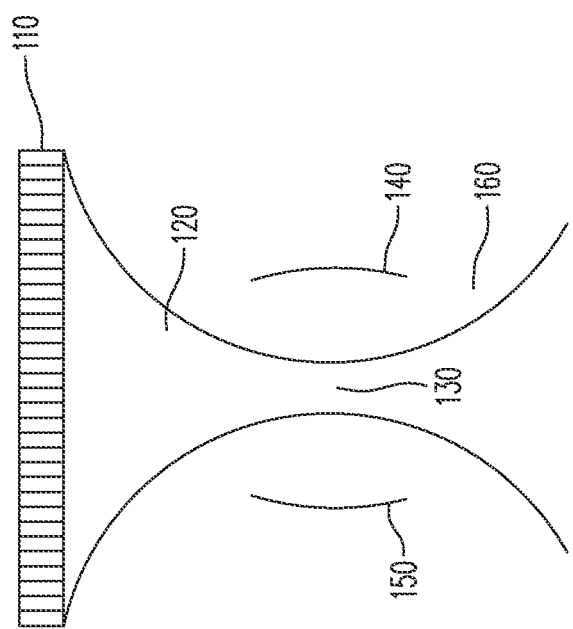
FIG. 1. A diagram of shear wave generation resulting from an acoustic radiation force.

Acoustic radiation force is created by a strong ultrasound pulse 120 as shown in FIG. 1. The ultrasound pulse 120 exhibits a high amplitude as well as a long duration, (e.g., on the order of 100 microseconds). The ultrasound pulse 120 is transmitted from an ultrasound transducer array 110. The ultrasound pulse 120 is focused at a focal point 130 in biological tissue 160, resulting in an acoustic radiation force which pushes the tissue 160 at the focal point 130. The ultrasound pulse 120 may be transmitted multiple times and may be focused at a different focal point for each of multiple transmitted ultrasound pulses.

The tissue 160 is pushed mostly in the axial direction of the ultrasound pulse 120, creating shear waves 140, 150 which may propagate in the lateral direction or directions other than the axial direction (i.e., vertical direction). The propagation velocity of the shear waves 140, 150 depends on the stiffness (Young's modulus or the shear modulus) of the tissue 160. Greater tissue stiffness results in greater shear wave propagation velocity as shown in equation 1. Pathological conditions such as cancer may increase tissue stiffness thus these conditions may be diagnosed by determining the propagation velocity. For example, the shear wave propagation velocity may vary from 1 m/s to 10 m/s, depending on tissue conditions.

Since the shear wave may be characterized by tissue movement (or motion), the shear wave may be detected by the ultrasound Doppler technique (e.g., see U.S. Pat. Nos. 4,573, 477, 4,622,977, 4,641,668, 4,651,742, 4,651,745, 4,759,375, 4,766,905, 4,768,515, 4,771,789, 4,780,837, 4,799,490, and 4,961,427). To detect this tissue movement (motion), the ultrasound pulse is transmitted multiple times to the tissue, and the ultrasound is scattered by scatterers in tissue and received by an ultrasound transducer as received ultrasound signals. The received ultrasound signals from the ultrasound array transducers are filtered, amplified, digitized, apotized, and beamformed (i.e. summed) after applying delays and/or phase-rotations for focusing and steering. The order of these processing steps may be interchanged. Received beamformed RF ultrasound signals undergo quadrature demodulation, resulting in complex, Doppler I-Q signals. In a color Doppler technique, the ultrasound is transmitted at a pulse repetition frequency (PRF) and the velocity is detected as the shift in frequency (Doppler shift frequency) in the received ultrasound signal. The received ultrasound is mixed with in-phase (0 degrees) and quadrature (90 degrees) reference signals of the same frequency as the transmitted ultrasound frequency, resulting in complex I-Q Doppler signals.

Generally, the complex I-Q signal is used to derive the Doppler shift frequency because the Doppler shift frequency and the blood velocity have the following relationship $$\Delta f = \frac{2 f_t v \cos\theta}{c_s}, \quad (2)$$

where $\Delta f$ is the Doppler shift frequency, $f_t$ is the transmitted frequency, $v$ is the blood velocity, $\theta$ is the angle between the ultrasound beam direction and the velocity vector, and $c_s$ is the speed of sound. The Doppler shift frequency is thus dependent on the angle between the velocity direction and the ultrasound beam direction and is a measurement that an ultrasound color Doppler system may obtain.

In the case of color Doppler, the number of the sampled signals may be limited to several. Therefore, an auto-correlation technique is usually used to determine the phase differences between the I-Q signals and then to determine the Doppler shift frequency and the velocity as follows. The color Doppler's I-Q signals z(m)=x(m)+jy(m) are used to calculate "auto-correlation" r as shown in the following equation, where z(m) is the complex I-Q Doppler signal, x(m) is the in-phase (real) signal, y(m) is the quadrature phase (imaginary) signal, m indicates the signal number, j is the imaginary unit and * indicates the complex conjugate.

$$r = \Sigma z(m) \cdot z^*(m-1) \quad (3)$$

The real (Re al(r)) and imaginary (Im ag(r)) parts of r are used to obtain the phase $\phi$ as shown in the following equation.

$$\varphi = \tan^{-1} \frac{\text{Imag}(r)}{\text{Real}(r)} \quad (4)$$

Since $\tan^{-1}$ usually provides only $-0.5\pi$ to $0.5\pi$, the position of complex value r in the complex coordinate may be also used to derive $\phi$ in the range of $-\pi$ to $\pi$. The phase (i.e., color Doppler phase) $\pi$ is then related to the Doppler shift frequency (i.e., color Doppler shift frequency) as shown in the following equation.

$$\Delta f = \frac{\varphi f_{PRF}}{2\pi} \quad (5)$$

Autocorrelation r between the received complex baseband ultrasound signals is thus obtained to detect tissue velocity or movement.

Tissue movement is detected at multiple lateral points in a field of tissue region by multiple ultrasound beams (for example, 540, 545, 550 in FIG. 5) in order to monitor movement. This movement reflects action of the shear wave at those multiple lateral points (or multiple ultrasound beams). Consequently, the lateral propagation velocity of the shear wave may be determined from the detected tissue movement.

Alternately, the shear wave may be detected by measuring tissue displacement caused by acoustic radiation force which is in turn caused by a strong ultrasound pulse as shown in FIG. 13. Tissue 1310 is positioned at a position 1320 before the acoustic radiation is applied and then is moved to a position 1330 after the acoustic radiation force was applied. To measure tissue displacement caused by the strong ultrasound pulse, ultrasound pulses are transmitted to tissue from an ultrasound transducer 1305 and then the ultrasound pulses are scattered from scatterers in tissue and returned to the transducer 1305 and received by the transducer 1305 as received ultrasound signals. The ultrasound pulses are focused at a depth in order to increase a signal-to-noise ratio of the resulting received ultrasound signals in comparison to unfocused ultrasound pulses. Using correlation of the received ultrasound signals from tissue the displacement 1340 (from the position 1320 to the position 1330) of the tissue 1310 due to the acoustic radiation force may be obtained and the tissue 1310 may be tracked thereafter. The ultrasound pulses may thereby track shear waves after shear waves are created by acoustic radiation force.

Ultrasound signals resulting from the first ultrasound pulse and received from the tissue 1310 before acoustic radiation force is applied are cross-correlated with received ultrasound signals resulting from the second ultrasound pulse after the acoustic radiation force is applied in order to find the best match between the received ultrasound signals. The best match may be found by finding a maximum correlation value to track the tissue and its displacement due to the acoustic radiation force. Therefore, when tissue displacement is observed or measured, a shear wave is detected. The displacement and tissue velocity may be related in that the displacement is a time integral $\int v_s dt$ of tissue velocity $v_s$. Therefore, the tissue displacement may be obtained by calculating the time integral of color Doppler velocity. Received ultrasound signals may be RF (Radio Frequency), IF (Intermediate Frequency) or baseband signals after demodulation. Alternately, the displacement may be further differentiated to obtain tissue strain, which may be then used to detect the shear wave propagation velocity.

Cross correlation $CC(t,\tau)$ of signals in the previous paragraphs may be mathematically expressed as follows, $$CC(t,\tau) = \int_t^{t+W} S_1(t') S_2(t'-\tau) dt' \qquad (6)$$

where $CC(t,\tau)$: cross correlation; $S_1(t')$: received signal from the first ultrasound transmission; $S_2(t'-\tau)$: received ultrasound signal from the second ultrasound transmission; W: window length; t: time; t': time; $\tau$: time displacement. Time displacement value r, which makes the maximum cross correlation (or the best match), determines the tissue displacement. Interpolation of signals using an interpolation function (e.g. cubic-spline) may be performed before cross correlation to increase spatial resolution.

The cross correlation may be replaced by the sum of absolute differences (SAD), the sum of square differences (SSD), the sum of absolute cubic differences (SCD), or the sum of absolute power differences (SPD) as follows.

$$SAD[l,k] = \sum_{n=0}^{N} |S_1[l+n] - S_2[l+n-k]| \qquad (7)$$

$$SSD[l,k] = \sum_{n=0}^{N} (S_1[l+n] - S_2[l+n-k])^2 \qquad (8)$$

$$SCD[l,k] = \sum_{n=0}^{N} |S_1[l+n] - S_2[l+n-k]|^3 \qquad (9)$$

$$SPD[l,k] = \sum_{n=0}^{N} |S_1[l+n] - S_2[l+n-k]|^p \qquad (10)$$

$S_1$ is the received ultrasound signal from the first ultrasound transmission before displacement, $S_2$ is the received ultrasound signal from the second ultrasound transmission after displacement. N: the number of signals in the signal window. k: window displacement by the number of signals and equivalent of $\tau$. l: the position of the window. p is a real number. For SAD, SSD, SCD and SPD, the tissue displacement is determined based on the value of k that makes the minimum (or best match) of each of the SAD, SSD, SCD and SPD.

In some embodiments, a color Doppler velocity, a color Doppler shift frequency or a color Doppler phase (as shown in equations 2, 3, 4 and 5) may be calculated based on the I-Q signals of the received ultrasound signals in order to determine tissue displacement as previously discussed. A time integral of the color Doppler velocity (or color Doppler shift frequency, color Doppler phase) yields the tissue displacement as previously described. The angle θ in equation 2 may be considered zero (0) degrees in this case.

FIGS. 8 and 9 are used to illustrate shear wave generation and detection in detail. A strong ultrasound pulse 820 is applied to tissue 860, 960 from an ultrasound transducer 810, 910 once or more times to increase the amplitude of shear waves which are caused by acoustic radiation forces resulting from the ultrasound pulse. Shear waves attenuate very quickly in tissue and thus a greater amplitude results in a greater propagation distance. One or multiple ultrasound pulses may be focused at one focal point or different focal points. The ultrasound pulse creates acoustic radiation forces which push a layer of tissue, resulting in tissue movement 830, 910 mostly in the axial (vertical) direction as illustrated in FIG. 9. The tissue layer movement 910 causes adjacent tissue layer movements 920, 925 mostly in the axial direction. The tissue layer movements 920, 925 then in turn cause next tissue layer movements 930, 935 which then cause adjacent tissue layer movements 940, 945. This succession of tissue movements represents a propagation of shear waves 840, 850 in the lateral (horizontal) direction as shown in FIG. 8. Since the tissue movements (or motions) caused by acoustic radiation forces are mostly in the axial direction, the motion may be detected by the color Doppler technique, which is sensitive to motions in the axial direction.

For example, the color Doppler technique transmits and receives several ultrasound pulses, determines phase differences between the received ultrasound signals, and calculates a velocity of tissue or blood using the autocorrelation technique as previously discussed and known in the art. Variance and power of color Doppler signals may be also calculated in addition to the velocity. As in the conventional display of moving tissue or blood, one of these parameters may be used to display shear waves as shown in FIGS. 10, 11. It will be assumed that shear waves 1040 (1140), 1050 (1150) are determined in a color Doppler frame representing a certain time and shear waves 1060 (1160), 1070 (1170) are determined at a next moment or in a next frame. More image frames of shear waves may be obtained to track the shear waves and to create a movie of shear wave propagation. In alternate embodiments, tissue displacement due to acoustic radiation forces may be detected.

FIGS. 10 and 11 depict shear wave propagation at two points in time. Local shear wave propagation velocities, as illustrated by arrows 1080, 1090, may be derived by correlating two images of shear waves at two points in time. More image frames of shear waves may be used to track the propagation of shear waves in more image areas in order to present local shear wave propagation velocities or shear wave propagation velocity squared in a two-dimensional image as described below.

Correlation coefficient (CCV) between a first frame signal $S^1$ and the second frame signal $S^2$ may be obtained as speckle tracking as follows, $$CCV(S^1, S^2) = \frac{\sum_{x=1}^{m}\sum_{z=1}^{n}(S_{x,z}^1 - \overline{S^1})(S_{x+X,z+Z}^2 - \overline{S^2})}{\sqrt{\sum_{x=1}^{m}\sum_{z=1}^{n}(S_{x,z}^1 - \overline{S^1})^2 \cdot \sum_{x=1}^{m}\sum_{x=1}^{n}(S_{x+X,z+Z}^2 - \overline{S^2})^2}} \qquad (11)$$

where $S^1_{x,z}$ is the ultrasound signal at x, z of the first frame, $S^2_{x+X,z+Z}$ is the ultrasound signal at x+X, z+Z of the second frame, $\overline{S^1}$ is mean signal value in the window of the first frame signal, $\overline{S^2}$ is mean signal value in the window of the second frame signal. The coordinate system (x, y, z) is shown with respect to an ultrasound transducer 1510 in FIG. 15. The elevational axis y is perpendicular to the paper of FIG. 15 although it is shown slightly different for illustration purposes.

The displacement X, Z, that yields the maximum correlation coefficient determines the correct speckle tracking and the distance, and thus the velocity (i.e., the to distance per time).

Similar to the 1D case, the correlation coefficient may be replaced by the sum of absolute differences (SAD), the sum of square differences (SSD), the sum of absolute cubic differences (SCD) and the sum of absolute power differences (SPD) as follows.

$$SAD(S^1, S^2, X, Z) = \sum_{x=1}^{m} \sum_{z=1}^{n} |S^1_{x,z} - S^2_{x+X,z+Z}| \quad (12)$$

$$SSD(S^1, S^2, X, Z) = \sum_{x=1}^{m} \sum_{z=1}^{n} (S^1_{x,z} - S^2_{x+X,z+Z})^2 \quad (13)$$

$$SCD(S^1, S^2, X, Z) = \sum_{x=1}^{m} \sum_{z=1}^{n} |S^1_{x,z} - S^2_{x+X,z+Z}|^3 \quad (14)$$

$$SPD(S^1, S^2, X, Z) = \sum_{x=1}^{m} \sum_{z=1}^{n} |S^1_{x,z} - S^2_{x+X,z+Z}|^p \quad (15)$$

p is a real number; m and n are integers. The 2D speckle tracking may be approximated by a 1D speckle tracking to obtain the shear wave propagation velocity and the shear wave propagation velocity squared. The mathematical expression will be similar to that used in the displacement measurement.

Figure 15:
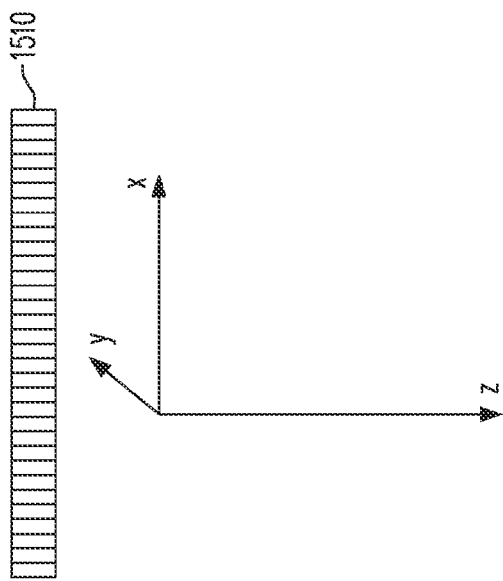
FIG. 15. A diagram to show an ultrasound coordinate system with respect to an ultrasound transducer.

Alternately, a shear wave equation (16) may be used to derive the shear wave propagation velocity as follows, $$\rho \frac{\partial^2 u_i}{\partial t^2} = \mu \left( \frac{\partial^2 u_i}{\partial x^2} + \frac{\partial^2 u_i}{\partial y^2} + \frac{\partial^2 u_i}{\partial z^2} \right) \quad (16)$$

where i=x, y, z, ρ is tissue density, μ is the shear modulus, $u_i$ is the displacement vector, x is lateral coordinate, y is elevational coordinate and z is axial coordinate as shown in FIG. 15. For incompressible materials, the Young's modulus E and the shear modulus μ have the following relationship.

$$E = 3\mu \quad (17)$$

Therefore, the shear wave propagation velocity squared may be obtained as a ratio of the shear modulus to the density as the following equation.

$$c^2 = \frac{\mu}{\rho} \quad (18)$$

One of the displacement components $u_z$ in equation 16 may be determined by cross-correlation as previously discussed. By combining z component of equation 16 and equation 18, the shear wave propagation velocity squared and velocity are obtained as follows, $$c^2 = \frac{\frac{\partial^2 u_z}{\partial t^2}}{\frac{\partial^2 u_z}{\partial x^2} + \frac{\partial^2 u_z}{\partial y^2} + \frac{\partial^2 u_z}{\partial z^2}} \quad (19)$$

and $$c = \sqrt{\frac{\frac{\partial^2 u_z}{\partial t^2}}{\frac{\partial^2 u_z}{\partial x^2} + \frac{\partial^2 u_z}{\partial y^2} + \frac{\partial^2 u_z}{\partial z^2}}} \quad (20)$$

Therefore, the shear wave propagation velocity is obtained as the square root of the ratio between the temporal second-order derivative of the displacement and the spatial second-order derivatives of the displacement. Likewise, the shear wave propagation velocity squared is obtained as the ratio between the temporal second-order derivative of the displacement and the spatial second-order derivatives of the displacement. Since the spatial derivative of the displacement in elevational direction $$\frac{\partial^2 u_z}{\partial y^2}$$

may be considered negligible compared with the other spatial derivatives, the shear wave propagation velocity squared and velocity may be obtained from the other measurement values.

Figure 5:
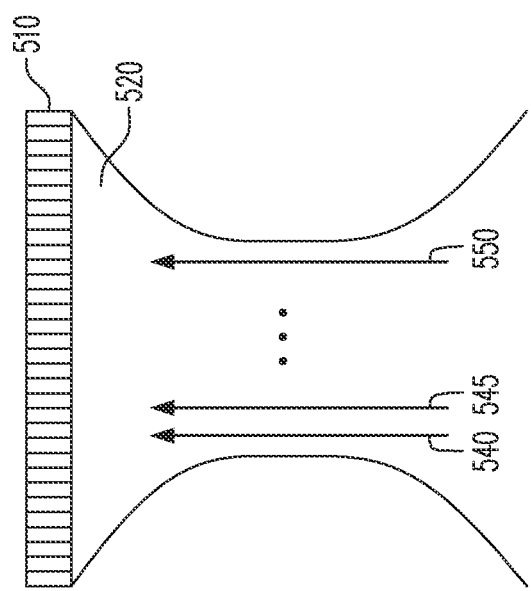
FIG. 5. A diagram of an ultrasound transmitted beam and multiple ultrasound received beams.

It is desirable to monitor and to track the shear wave frequently, meaning at a fast rate or frame rate. To speed up the frame rate, a wide, focused ultrasound pulse 520 may be transmitted and multiple ultrasound signals 540, 545, 550 may be simultaneously received as shown in FIG. 5. The received ultrasound beams are used as described previously to detect shear waves and to derive shear wave propagation properties (i.e., velocity and velocity squared) therefrom. The focused transmit ultrasound beam 520 may be particularly suitable for maintaining a good signal-to-noise ratio of resulting received ultrasound beams during the detection of shear waves.

Figure 4:
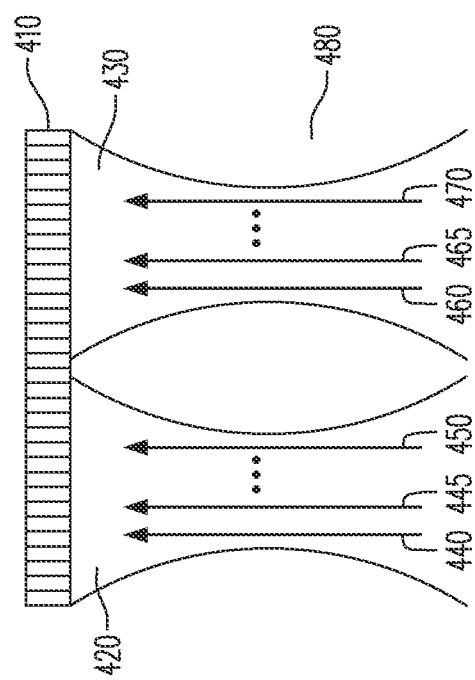
FIG. 4. A diagram of multiple ultrasound transmitted/received beams.

In some embodiments, multiple ultrasound beams (pulses) are simultaneously applied and transmitted to the tissue field and multiple ultrasound beams (pulses) per transmitted ultrasound pulse are received to increase the frame rate, as shown in FIG. 4. In FIG. 4, ultrasound pulses 420, 430 are simultaneously transmitted to biological tissue 480 from an ultrasound transducer array 410. For each transmitted ultrasound pulse 420, 430, multiple ultrasound receive signals 440, 445, 465, 460, 465, 470 are simultaneously received. The multiple ultrasound pulses may be transmitted simultaneously or at substantially simultaneous times. The multiple ultrasound pulses may be simultaneously transmitted. Or a second ultrasound pulse may be transmitted after a first ultrasound pulse is transmitted and before the first ultrasound pulse returns to the ultrasound transducer from a deepest depth of an ultrasound field. This transmission method increases the frame rate.

FIG. 4 shows an example of two simultaneous transmitted ultrasound pulses but more than two transmitted ultrasound pulses may be also used. In some embodiments, coded ultrasound waveforms may be transmitted for better separation of simultaneous multiple ultrasound signals. For example, chirp codes, Barker codes, Golay codes or Hadamard codes may be used for better separation of ultrasound pulses. Again, the received signals are analyzed using the methods previously described to determine tissue movement at multiple points, and shear wave propagation properties are derived therefrom.

An image of a shear wave can be created based on the motion (or velocity) detected at multiple points in the imaging field. Subsequent transmit/receive sequences of ultrasound may create multiple images of the shear wave at multiple points in time. Correlation between the images of the shear wave is then calculated to obtain the shear wave propagation velocity and velocity squared as previously discussed. Alternately, tissue displacement caused by acoustic radiation force is determined and the shear wave propagation velocity is calculated as the square root of the ratio between the temporal second-order derivative of the displacement and the spatial second-order derivatives of the displacement. Likewise, the shear wave propagation velocity squared is calculated as the ratio between the temporal second-order derivative of the displacement and the spatial second-order derivatives of the displacement.

In some embodiments, the propagation velocity of a detected shear wave (c) may be displayed. In some embodiments, the propagation velocity squared ($c^2$) of the detected shear wave may be displayed. Advantageously, the propagation velocity squared ($c^2$) may be more closely related than the propagation velocity (c) to the Young's modulus or the shear modulus as shown in equation 1. Therefore the propagation velocity squared ($c^2$) may provide an efficient proxy for the actual stiffness. In some embodiments, the propagation velocity squared ($c^2$) may be multiplied by three and then displayed. If tissue density is close to 1 g/cm$^3$, this number (i.e., $3c^2$) may be close to the actual Young's modulus. In some embodiments, a product ($bc^2$) of any real number (b) and the propagation velocity squared ($c^2$) may be displayed. Determinations of actual stiffness are difficult and error-prone because the density of the tissue is unknown and must be estimated.

A color coding technique, a grayscale technique, or a graphical coding technique may be employed to present a shear wave propagation property (i.e., velocity c or velocity squared $c^2$) to a user. In some embodiments, a propagation velocity squared ($c^2$) of shear waves within tissue is displayed in a two-dimensional color image. Graphical-coding and/or two-dimensional images may also be used to represent the propagation velocity c or velocity squared $c^2$ in some embodiments.

A low value of shear wave propagation velocity squared $c^2$ may be coded using a red color while a high value of $c^2$ may be coded using a blue color. For example, FIG. 6 illustrates a legend indicating that a red-colored tissue area includes shear waves associated with low $c^2$ values (e.g., 1 m$^2$/s$^2$) and that a blue-colored tissue area includes shear waves associated with high $c^2$ values (e.g., 100 m$^2$/s$^2$). Embodiments are not limited to color-based coding. Images of shear wave propagation properties within tissue may be coded using grayscale or any combination of graphical patterns (e.g., vertical lines, horizontal lines, cross-hatching, dot patterns of different densities, etc.) and colors.

After determining the propagation velocity squared ($c^2$), $c^2$ may be coded linearly with respect to the color wavelength as shown in FIG. 6. For example, if $c^2$ within a tissue area is determined to be 50 m$^2$/s$^2$, the tissue area may be displayed using a yellow color 630.

Alternately, color-coding of the shear wave propagation velocity squared ($c^2$) may be defined as shown in FIG. 7. Tissue areas associated with low values of the shear wave propagation velocity squared may be displayed as blue 710 while areas associated with high values of the velocity squared may be displayed as red 720. Different color-coding methods may be also used to represent the propagation velocity squared ($c^2$) or velocity c of shear waves. For example, color coding may be based on hue, brightness, and other color characteristics. The color-coded scale may represent different maximums and minimums of the shear wave propagation velocity squared or velocity than shown in FIG. 6, 7. In this regard, the velocity squared maximum of 100 m$^2$/s$^2$ and velocity squared minimum of 1 m$^2$/s$^2$ in FIGS. 6 and 7 are only for the illustration purposes and do not limit the scope of the claims. Other values may represent the maximum or minimum values of the coding scale.

Figure 14:
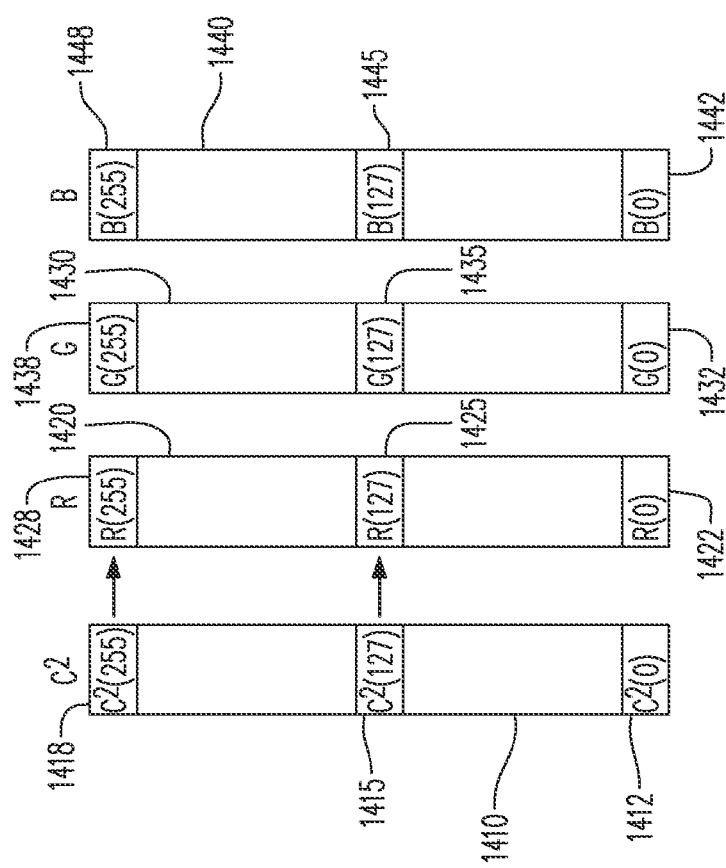
FIG. 14. Scale of shear wave velocity squared $c^2$ by color coding bar composed of RGB representation.

Color coding based on Red, Green and Blue (RGB) values may be used to represent the propagation velocity c or velocity squared ($c^2$) of shear waves as shown in FIG. 14. In this example (FIG. 14), the propagation velocity squared ($c^2$) of a shear wave within tissue is represented according to a color coding bar 1410 which is based on RGB values 1420, 1430 and 1440. The shear wave propagation velocity squared has 256 possible values in this example, as represented 256 colors in the color coding bar 1410. The smallest velocity squared $c^2(0)$ 1412 is represented by a color composed of a combination of R(0) 1422, G(0) 1432 and B(0) 1442. The middle velocity squared $c^2(127)$ 1415 is represented by a color composed of a combination of R(127) 1425, G(127) 1435 and B(127) 1445. The highest velocity squared $c^2(255)$ 1418 is represented by a color composed of a combination of R(255) 1428, G(255) 1438 and B(255) 1448. In this example, R(255) only indicates a Red color associated with the red index 255 and does not necessarily indicate a Red color value of 255, which is the brightest Red color. Likewise, G(255) indicates a Green color associated with the green index 255 and B(255) indicates a Blue color associated with the blue index 255.

Alternately, Red, Green, Blue and Yellow may be used to define a color coding bar. Alternately, a Hue-based color coding bar may be used.

FIG. 12 represents an example of a color-coded image 1260 displaying a shear wave propagation velocity squared $c^2$ within human soft tissue (e.g. breast). A color coding scale 1250 is illustrated, in which a color code 1210 (i.e., representing a red color although displayed as white in this black/white document) represents a low shear wave propagation velocity squared value and a color code 1220 (i.e., representing a blue color although displayed as hatched in this black/white document) represents a higher shear wave propagation velocity squared value.

Based on the coding scale 1250, it can be seen that the color coded image 1260 includes an area 1280 of high propagation velocity squared $c^2$. Since the shear wave propagation velocity squared $c^2$ is proportional to the Young's modulus, the tissue area corresponding to area 1280 is likely to be hard. Since a tumor is generally hard, image 1260 may indicate pathological conditions.

The color-coding method provides efficient distinction between an area including shear waves having a high propagation velocity squared value and other areas including shear waves having a low propagation velocity squared value. The color coding method therefore allows efficient identification of hard tissue areas within soft tissue areas. An image displaying shear wave propagation velocity or velocity squared may be combined (e.g., superimposed) with a regular image of ultrasound, e.g. B-mode image, or a combined B-mode image and color Doppler image and/or spectral Doppler image. Alternately, the shear wave propagation velocity squared or velocity may be displayed numerically. In some embodiments, the shear wave propagation velocity squared may be displayed in gray scale or based on other graphic coding methods such as using patterns rather than colors. For example, low values of shear wave propagation velocity or square of the shear wave propagation velocity may be displayed in black or dark gray while high values of shear wave propagation velocity or shear wave propagation velocity squared may be displayed in light gray or white using a grayscale coding method.

Figure 19A:
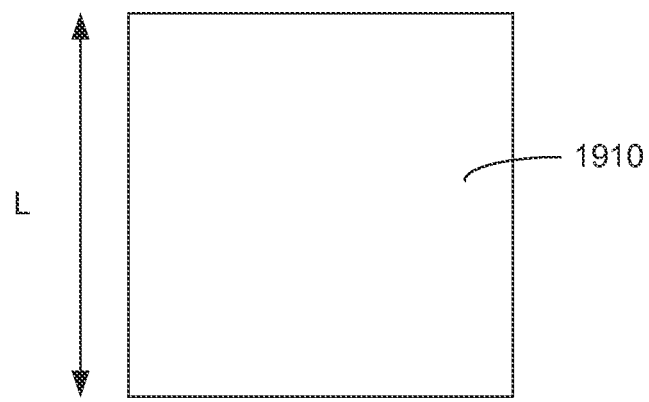
FIG. 19A. Tissue before compression.
Figure 19B:
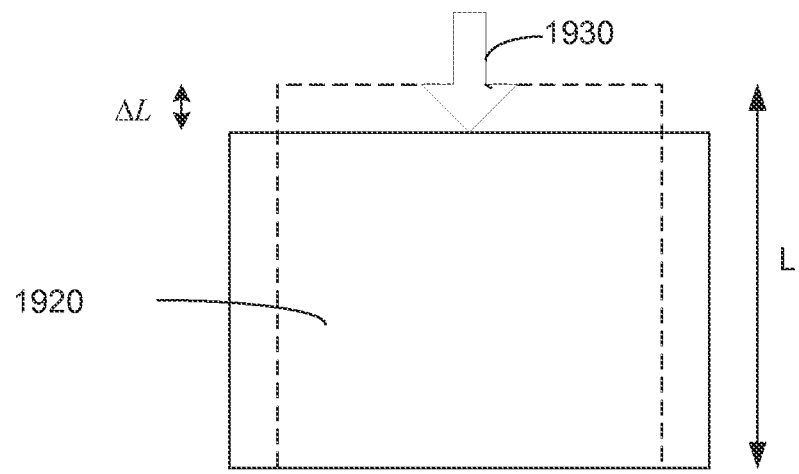
FIG. 19B. Tissue after compression.

Tissue strain ε is a measure of tissue displacement as follows, $$\sigma = E\varepsilon \quad (21)$$

$$\sigma = E\frac{\Delta L}{L} \quad (22)$$

$$\varepsilon = \frac{\Delta L}{L} \quad (23)$$

where σ is stress, E Young's modulus, L tissue length, ΔL displacement as shown in FIGS. 19A and 19B. FIG. 19A illustrates tissue 1910 and its length L before a force 1930 was applied while FIG. 19B shows the tissue 1920 after the force 1930 was applied and the tissue 1920 was compressed. The stress σ is a force per area and is related to the strain σ via the Young's modulus E as shown in equation 21. The force may be a mechanical force from pushing an ultrasound probe into the tissue or an acoustic radiation force created by a transmit ultrasound pulse. Equation (22) may be re-written for a local strain $$\frac{\partial u_z}{\partial z},$$

instead of a global strain $$\frac{\Delta L}{L}$$

(i.e., mean strain over the length L).

$$\sigma = E\frac{\partial u_z}{\partial z} \quad (24)$$

where $u_z$ is a local displacement at an axial position z using the convention introduced in equation 16. Therefore, the spatial derivative of the displacement is a strain or a local strain which may vary from one position to another position. Likewise, the stress may vary from one position to another position. As tissue stress or compression increases, tissue strain increases. For a given stress, strain is smaller if the tissue stiffness is harder and Young's modulus is larger. Therefore, tissue strain may indicate tissue stiffness as long as the stress is known. However, in general stress may not be readily available. Therefore strain may indicate relative tissue stiffness in an area of similar stress and thus may be considered qualitative. Stress and thus strain may be created by acoustic radiation forces previously discussed or mechanical compression by an ultrasound probe. On the other hand, shear wave propagation velocity or velocity squared are more directly related to tissue stiffness because the tissue density may be relatively constant in equation 1. Thus shear wave propagation velocity or velocity squared may directly indicate tissue stiffness and Young's modulus and thus may be considered quantitative. However, the shear wave velocity imaging requires shear wave detection at 2 or more lateral positions or 2 or more ultrasound beams and thus may have a limited lateral resolution. On the other hand, strain may be obtained over one ultrasound beam and thus may have better lateral resolution than shear wave velocity imaging. Therefore in this embodiment, a new shear wave velocity image is created using both strain imaging and shear wave velocity imaging data.

Figure 16A:
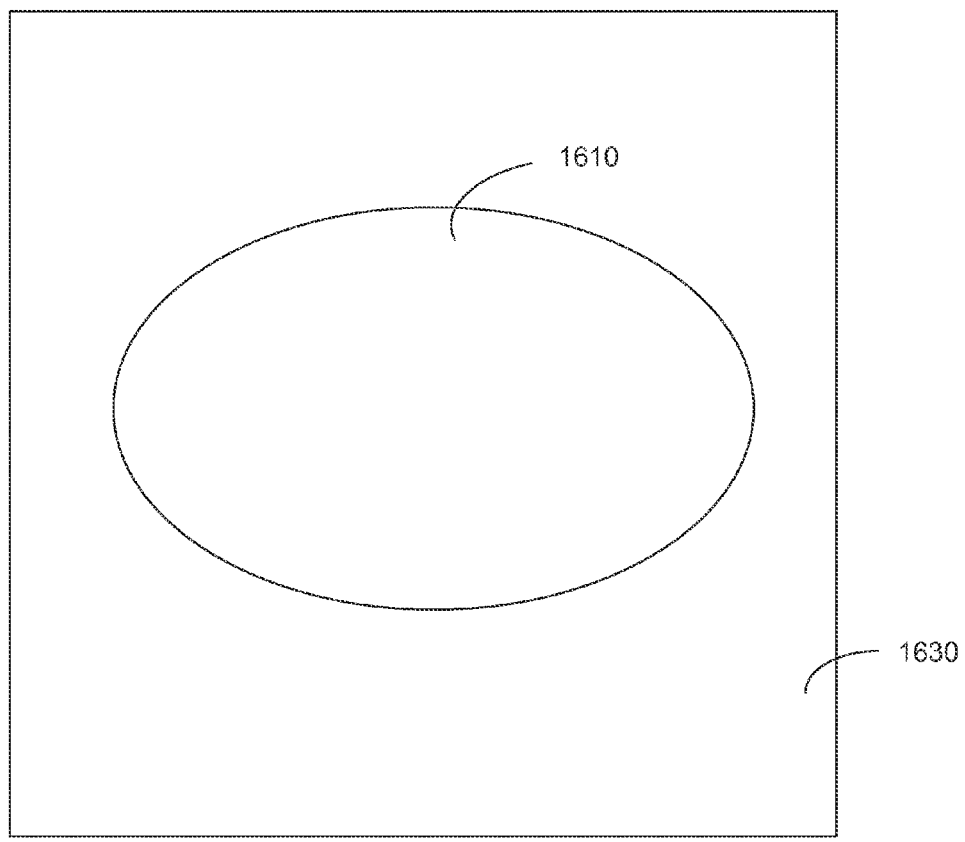
FIG. 16A. Strain image.
Figure 16B:
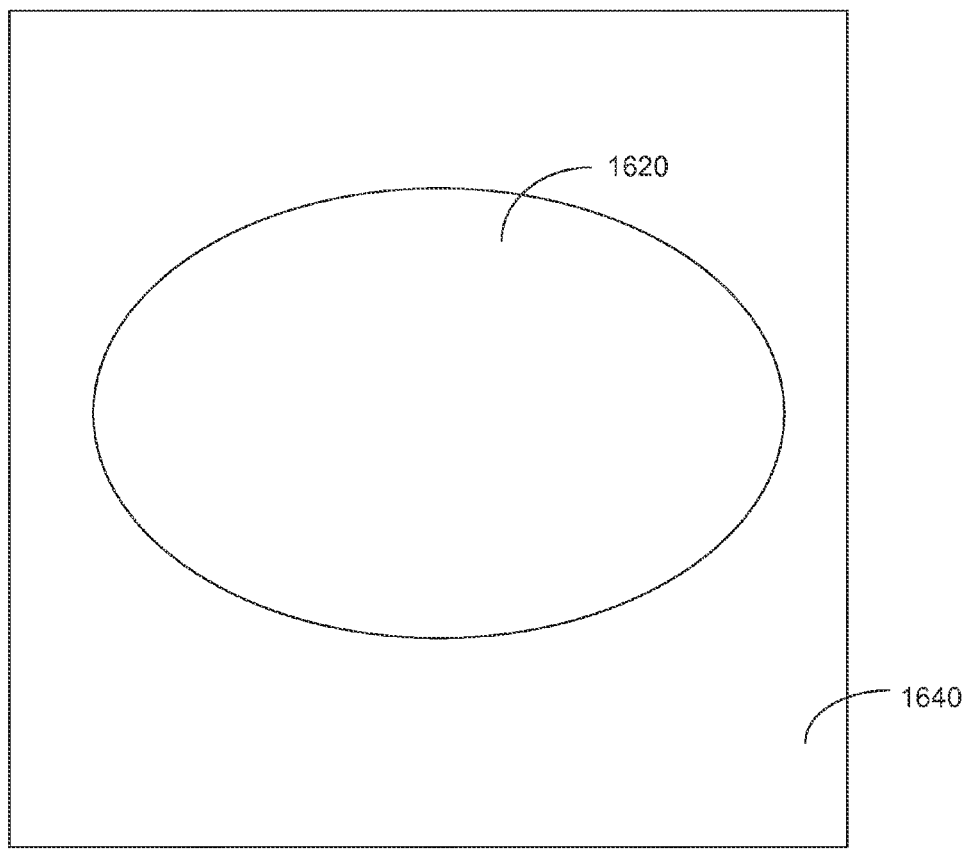
FIG. 16B. Shear wave image.

First, a shear wave velocity image 1640 is obtained as previously discussed and shown in FIG. 16B. Second, a strain image 1630 is created either by acoustic radiation forces or mechanical compression, e.g. by an ultrasound probe, and is shown in FIG. 16A. An ultrasound image is obtained from tissue as a reference image before forces, i.e., acoustic radiation forces or mechanical compression, are applied as shown in FIG. 19A. The second ultrasound image is acquired after the forces, i.e., acoustic radiation forces or mechanical compression, are applied as shown in FIG. 19B. Tissue displacement is calculated by correlation of the two (first and second) images (FIGS. 19A and 19B). For example, equations 6, 7, 8, 9 or 10 may be applied to the two images obtain a correlation and thus a displacement $u_z$. The spatial derivative of the displacement $$\frac{\partial u_z}{\partial z}$$

yields a strain image.

Figure 16C:
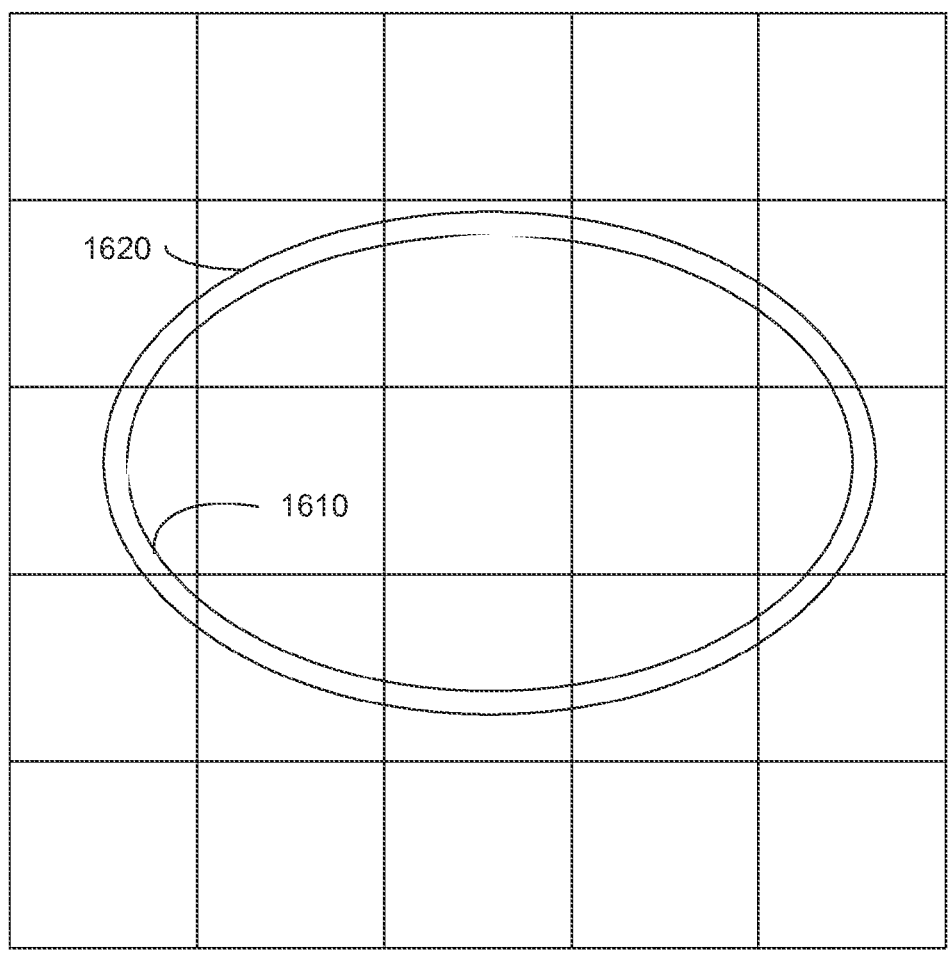
FIG. 16C. Strain image and shear wave image.
Figure 17:
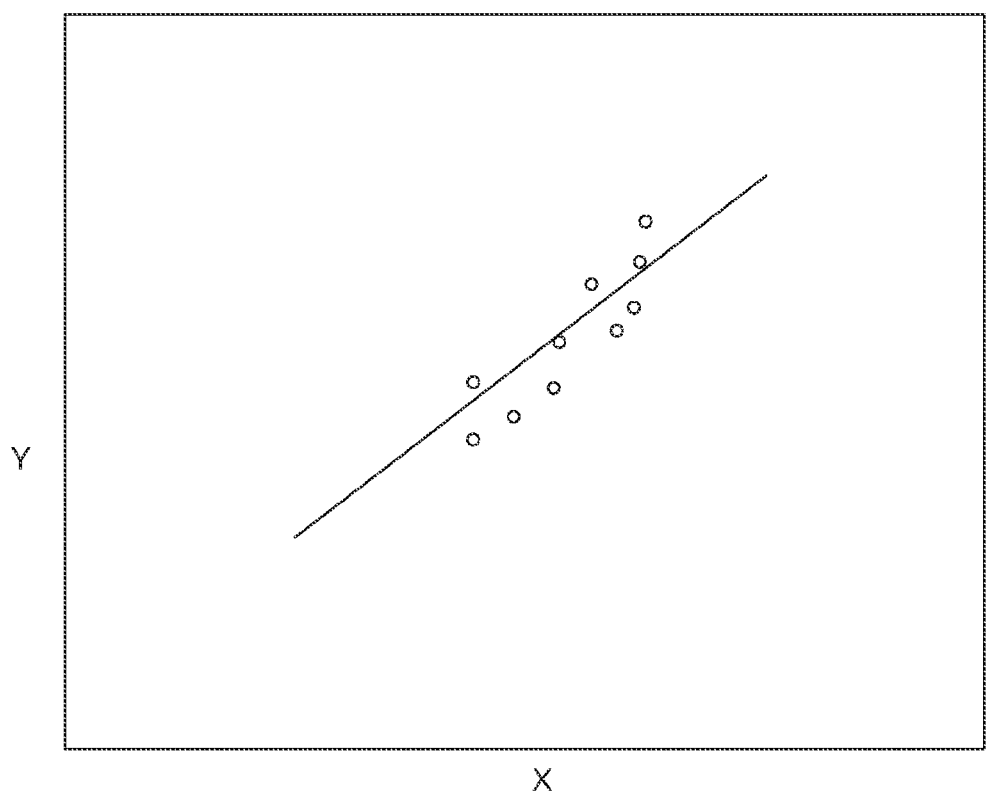
FIG. 17. Correlation and a regression line between shear wave image values and strain image values according to some embodiments.

Third, both strain 1630 and shear wave velocity images 1640 are partitioned (divided) to multiple matched areas as shown in FIG. 16C. This process is performed because the stress may vary from one position to another as previously discussed. In FIG. 16C, the two images (i.e. strain image 1630, shear wave image 1640) are superimposed on each other to depict their spatial relationship. The slightly larger elliptical image 1620 depicts a tumor imaged by the shear wave imaging while the smaller elliptical image 1610 represents the tumor imaged by the strain imaging, indicating different spatial resolution. Fourth, each strain image value (horizontal axis) of each pixel point in an area is plotted against the shear wave image value (vertical axis) of each same (corresponding) pixel point in the area as shown in FIG. 17. Fifth, a regression line (e.g. a straight line or a curved line) or regression line equation (e.g., Y=aX+b, where X represents strain image value while Y represents shear wave image value) and a correlation coefficient are obtained between the strain image values and the shear wave image values as shown in FIG. 17, i.e. the square of shear wave propagation velocity and the inverse of strain at each corresponding pixel position in each area as shown in FIG. 16C. The regression line is a line to closely relate variables X and Y by minimizing errors. Variable X ($X_i$: actual shear data samples) and variable Y ($Y_i$: actual strain data samples) at a given image point (pixel) are assumed related by a regression line; e.g. Y=aX+b and a and b are obtained to minimize the sum of errors (e.g., square errors) as follows, $$\Sigma(Y_i - aX_i - b)^2 \quad (25)$$

where an error is a difference between the estimated Y value $Y_{est}$ by the regression line for a given $X_i$ using the regression line and the actual data sample $Y_i$, as follows, $$Y_{est} = aX_i + b \quad (26)$$

$$\text{Error} = Y_i - Y_{est} \quad (27).$$

From equation (1), (21) and (24), assuming a constant stress in a small area, the square of shear wave propagation velocity is proportional to the inverse of the strain as follows, $$c^2 \propto \frac{1}{\varepsilon}. \tag{28}$$

Alternately, the strain may be proportional to the inverse of the square of shear wave propagation velocity as follows.

$$\varepsilon \propto \frac{1}{c^2} \tag{29}$$

where, $\varepsilon$ is the strain and c is the shear wave propagation velocity. Therefore, in a small area where a constant stress is expected, a linear correlation may be expected as shown in FIG. 17.

In some embodiments, in addition to actual data, virtual data at the origin (0, 0) may be used for the calculation of a regression line because of the relationship between the square of the shear wave velocity and the strain.

The correlation coefficient r between data samples $X_i$ and data samples $Y_i$ is obtained as follows, $$r = \frac{\sum_{i=1}^{n}(X_i - \overline{X})(Y_i - \overline{Y})}{\sqrt{\sum_{i=1}^{n}(X_i - \overline{X})^2}\sqrt{\sum_{i=1}^{n}(Y_i - \overline{Y})^2}} \tag{30}$$

where $\overline{X}$ and $\overline{Y}$ are mean of $X_i$ and $Y_i$, respectively.

If the correlation coefficient in one of the areas is greater than a preset value (i.e., a threshold), the strain image values in that area are converted to the square of shear wave velocity using the regression line by inputting X (i.e., a strain image value) in the regression line equation and calculating the resulting new shear wave velocity (or velocity squared) (i.e., Y) image value. Since the strain image values are used to create the new shear wave image values for the area, the new shear wave image should have the same spatial resolution as the strain image, which is greater than the spatial resolution of the original shear wave image.

If the correlation coefficient is lower than the threshold for an area, the strain image values and shear wave image values for the area are not well correlated. This may occur in areas of large stiffness changes, e.g., at the border of stiff tissue areas. If the correlation coefficient is lower than the preset value, a regression line of the nearest neighboring area associated with a correlation coefficient greater than the preset value is used as described above to convert strain image values of the current area to shear wave image values.

Figure 18:
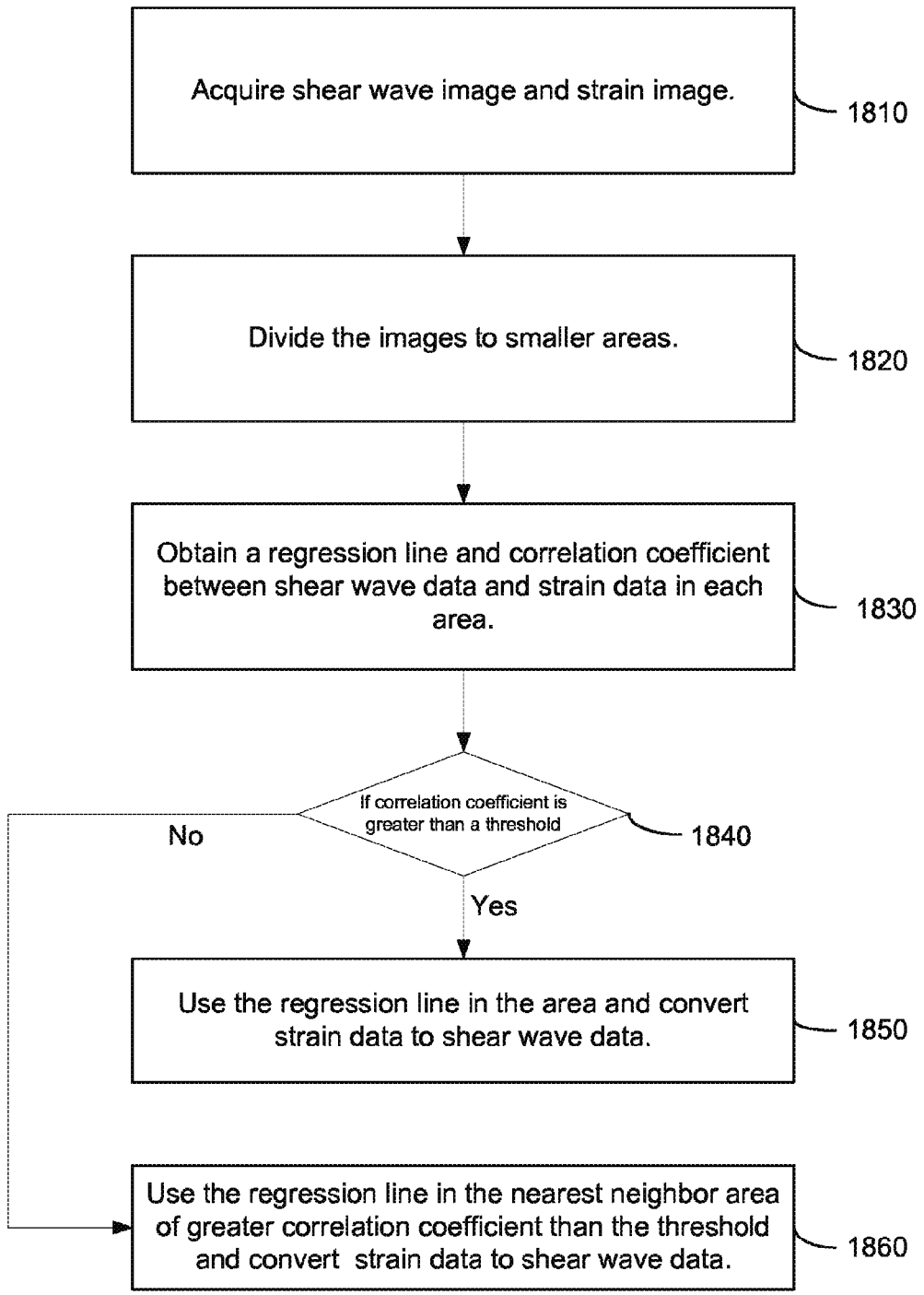
FIG. 18. Flow chart of a process according to some embodiments.

Overall flow is shown in FIG. 18. A shear wave image (either velocity or velocity squared) and a strain image are acquired at 1810. The images are divided into smaller areas at 1820. A regression line and a correlation coefficient are obtained at 1830 for each smaller area based on the shear wave image values (e.g., shear wave velocity or velocity squared) and strain image values (e.g. strain, inverse of strain) of the smaller area. If the correlation coefficient for an area is determined to be greater than a threshold at 1840, the strain image values of the area are converted to shear wave image values of the area using the regression line at 1850. If the correlation coefficient for the area is not greater than the threshold, the strain image values are converted at 1860 to shear wave image values using a regression line of the nearest neighboring area having a correlation coefficient greater than the threshold.

In some embodiments, smaller areas may be made from the strain and shear wave images rather than dividing (partitioning) the images as shown in FIG. 16C. In other words, there may be a gap between neighboring areas. FIG. 16C represents the case without any gap. All or some of shear wave or strain pixels in each area may be used for the calculation of the correlation coefficient and the regression line.

Figure 20:
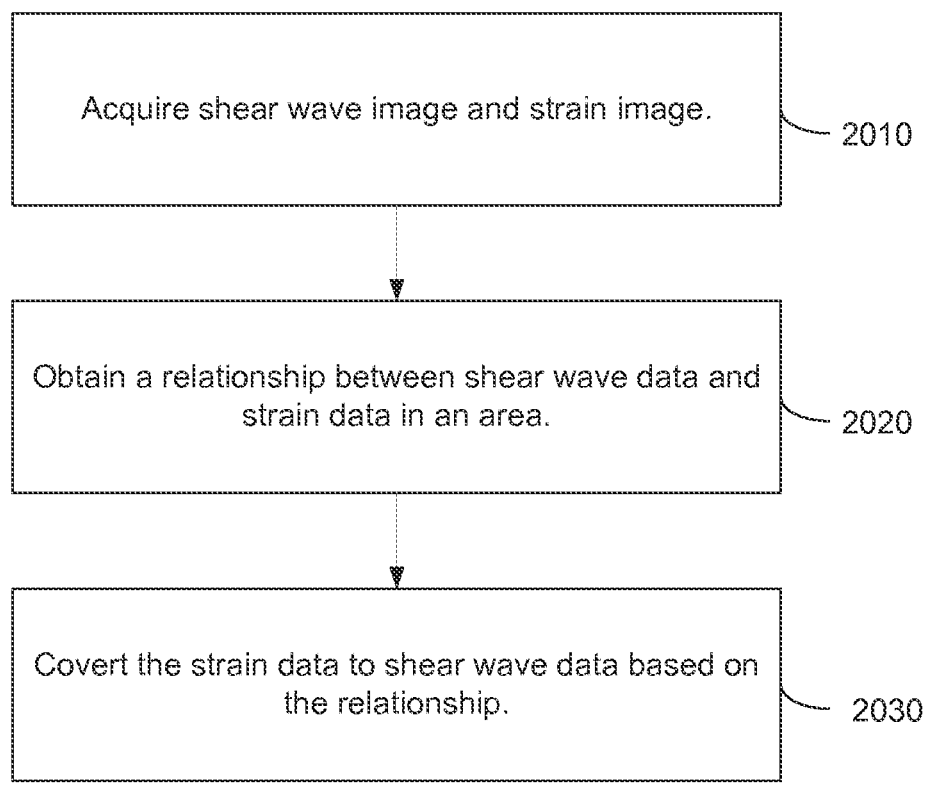
FIG. 20. Flow chart of a process according to some embodiments.

In some embodiments, a small area is selected in a strain image and a shear wave. A relationship (e.g., a regression line and/or a correlation coefficient) is obtained between strain image values and shear wave image values in the area. Then the strain image values are converted to shear wave image values based on the relationship. This procedure may be repeated in another small area to cover all or part of the images. The strain image is thus converted a new shear wave image in all or part of the original image area. FIG. 20 illustrates the flow of the processing. First, a shear wave and strain images are acquired at 2010. A relationship (e.g. a regression line and/or a correlation coefficient) is obtained in an area at 2020. Strain image data are converted to shear wave image data using the relationship at 2030.

In some embodiments, strain image data are converted to shear wave image data using the regression line without checking the correlation coefficient.

In some embodiments, an area is adaptively selected where correlation between the shear wave image data and strain image data is high. In other words, an area is searched where correlation between shear wave image data and strain image data is higher than a threshold. In this area, the regression line is obtained and the strain image data are converted to shear wave image data using the regression line. This process may be repeated in another area. This is effective to find an area of the same stress and to exclude areas of large stress variation, e.g. borders of hard tissue lesions (or tumors) as shown in FIG. 16C.

In some embodiments, shear wave image values may be converted to strain image values based on the regression line. The detailed process follows. A first shear wave image is acquired. A strain image is acquired. The strain image and the first shear wave are divided into plural areas. A regression line between the strain image values and the first shear wave image values in each area of the plural areas is calculated. The strain image values are converted to shear wave values based on the regression line in each area.

In some embodiments, a shear wave image and/or strain image may consist of a few pixels to billions of pixels. In some embodiments, a shear wave image and/or strain image may consist of at least one image pixel.

In the previous discussion, two-dimensional images are used to describe the embodiments. However, the processes described herein may be applied to three-dimensional images, in which the images are divided into volumes, instead of areas, at 1820.

Figure 3:
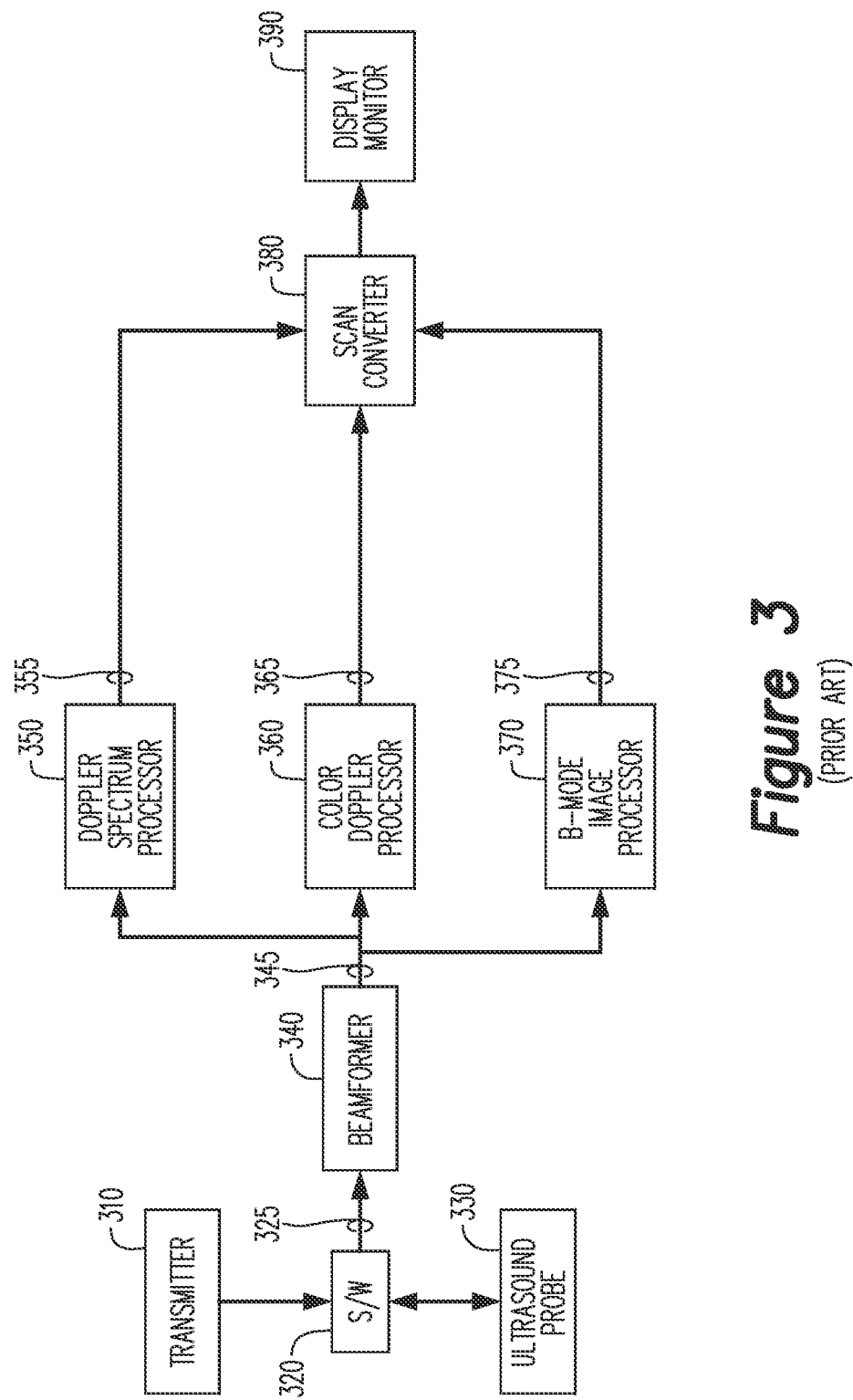
FIG. 3. A diagram of a conventional ultrasound imaging system.

FIG. 3 shows a diagram of a conventional ultrasound diagnostic imaging system with B-mode imaging, Doppler spectrum and color Doppler imaging. The system may include other imaging modes, e.g. elasticity imaging, 3D imaging, real-time 3D imaging, tissue Doppler imaging, tissue harmonic imaging, contrast imaging and others. An ultrasound signal is transmitted from an ultrasound probe 330 driven by a transmitter/transmit beamformer 310 through a transmit/receive switch 320. The probe 320 may consist of an array of ultrasound transducer elements which are separately driven by the transmitter/transmit beamformer 310 with different time-delays so that a transmit ultrasound beam is focused and steered. A receive beamformer 340 receives the received ultrasound signals from the probe 330 through the switch 320 and processes the signals 325. The receive beamformer 340 applies delays and/or phases to the signals and the resultant signals are summed for focusing and steering a received ultrasound beam. The receive beamformer 340 may also apply apodization, amplification and filtering.

The processed signal 345 is coupled to a Doppler spectrum processor 350, a color Doppler processor 360, and a B-mode image processor 370. The Doppler spectrum processor 350 includes a Doppler signal processor and a spectrum analyzer, and processes Doppler flow velocity signals and calculates and outputs a Doppler spectrum 355. The color Doppler processor 360 processes the received signal 345 and calculates and outputs velocity, power and variance signals 365. The B-mode image processor 370 processes the received signal 345 and calculates and outputs a B-mode image 375 or the amplitude of the signal by an amplitude detection.

The Doppler spectrum signals 355, color Doppler processor signals (velocity, power, and variance) 365 and B-mode processor signals 375 are coupled to a scan converter 380 that converts the signals to scan-converted signals. The output of scan converter 380 is coupled to a display monitor 390 for displaying ultrasound images.

Figure 2:
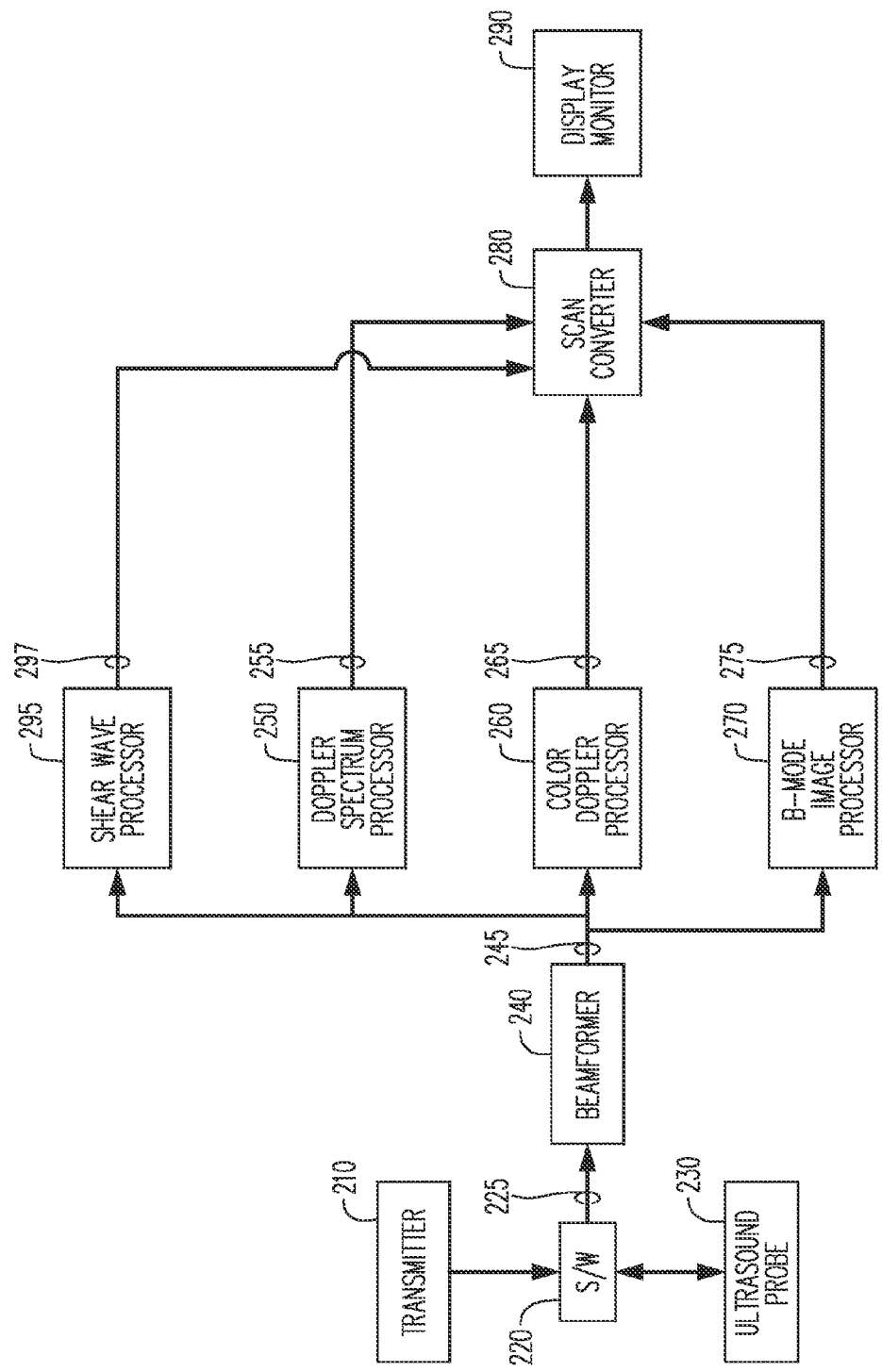
FIG. 2. A diagram of an ultrasound imaging system of some embodiments.

FIG. 2 shows a diagram of elements of an ultrasound imaging system including a shear wave/strain processor 295 according to some embodiments. The ultrasound system in FIG. 2 transmits strong ultrasound pulses to biological tissue to create acoustic radiation forces which push the biological tissue. Shear waves are created and propagate in the tissue after the biological tissue is pushed. The ultrasound system then transmits and receives ultrasound pulses to track the shear waves as the shear waves propagate in the biological tissue. Multiple received ultrasound beams may be simultaneously formed by the receive beamformer 240. Likewise, multiple transmitted ultrasound beams may be simultaneously formed by the transmitter/transmit beamformer 210. Received ultrasound signals from the receive beamformer 240 are processed to obtain tissue displacement, Doppler velocity, correlation, shear wave propagation velocity and/or shear wave propagation velocity squared as previously described. The shear wave/strain processor 295 may perform the shear wave and strain processing methods described previously. The shear wave/strain processor 295 receives output 245 from the receive beamformer 240. Output 297 comprises shear wave velocity data or other shear wave properties. For example, the shear wave/strain processor 295 outputs the propagation velocity or the square of the propagation velocity of the shear wave to a scan converter 280 and a representation of the shear wave propagation velocity or the square of the shear wave propagation velocity is output to the display monitor along with the B-mode, color Doppler or spectral Doppler images.

The shear wave/strain processor 295 may comprise of general purpose central processing units (CPUs), digital signal processors (DSPs), field programmable Arrays (FPGAs), graphic processing units (GPUs) and/or discreet electronics devices.

FIG. 2 represents a logical architecture according to some embodiments, and actual implementations may include more or different elements arranged in other manners. Other topologies may be used in conjunction with other embodiments. Moreover, each element of the FIG. 2 system may be implemented by any number of computing devices in communication with one another via any number of other public and/or private networks. Two or more of such computing devices may be located remote from one another and may communicate with one another via any known manner of network(s) and/or a dedicated connection. The system may comprise any number of hardware and/or software elements suitable to provide the functions described herein as well as any other functions. For example, any computing device used in an implementation of the FIG. 2 system may include a processor to execute program code such that the computing device operates as described herein.

All systems and processes discussed herein may be embodied in program code stored on one or more non-transitory computer-readable media. Such media may include, for example, a floppy disk, a CD-ROM, a DVD-ROM, a Blu-ray disk, a Flash drive, magnetic tape, and solid state Random Access Memory (RAM) or Read Only Memory (ROM) storage units. The program code may be executed by one or more computing devices to perform any of the processes described herein. In this regard, the one or more computing devices may also include one or more memory devices (e.g., RAM or ROM storage units) to store the program code prior to execution thereof. Embodiments are therefore not limited to any specific combination of hardware and software.

One or more embodiments have been described. Nevertheless, various modifications will be apparent to those in the art.

The invention claimed is:

1. A method comprising:
acquiring a first shear wave image of at least one shear wave propagation property;
acquiring a strain image;
dividing the strain image and the first shear wave image into plural areas;
calculating a regression line between values of the strain image and values of the first shear wave image in each area of the plural areas; and
converting the strain image to a second shear wave image of at least one shear wave propagation property based on the regression line.

2. A method according to claim 1, wherein acquiring the strain image comprises acquiring the strain image by using forces of acoustic radiation forces or mechanical compression.

3. A method according to claim 1, wherein the first shear image comprises of at least one image pixel.

4. A method according to claim 1, wherein the strain image values comprise the strain or the inverse of strain.

5. A method according to claim 1, wherein acquiring a shear wave image comprises:
applying a first ultrasound pulse to biological tissue to create shear waves in the biological tissue;
transmitting a focused ultrasound pulse into the biological tissue;
receiving one or more ultrasound signals from the biological tissue generated in response to the focused ultrasound pulse;
detecting the shear waves in the biological tissue based on the received one or more ultrasound signals;
determining at least one shear wave propagation property associated with the detected shear waves; and
forming a first shear wave image of the at least one shear wave propagation property associated with the detected shear waves.

6. A method according to claim 2, wherein acquiring the strain image by using the forces comprises:
acquiring a first ultrasound image before the forces are applied to the biological tissue;

acquiring a second ultrasound image after the forces are applied to the biological tissue;

calculating tissue displacements between the first and second ultrasound images by a cross correlation, a sum of absolute differences (SAD), a sum of square differences (SSD), a sum of absolute cubic differences (SCD), a sum of absolute power differences (SPD), a color Doppler shift frequency, a color Doppler phase or a color Doppler velocity; and calculating the strain image by calculating a spatial derivative of the displacements.

7. A method according to claim 1, wherein the at least one shear wave propagation property comprises one or more of;
   a propagation velocity associated with one or more of the detected shear waves; and
   a product ($bc^2$) of a real number (b) and the square of the shear wave propagation velocity ($c^2$).

8. A non-transitory medium storing computer-executable program code, the program code executable by a computing device to:
   acquire a first shear wave image of at least one shear wave propagation property;
   acquire a strain image;
   divide the strain image and the first shear wave image into plural areas;
   calculate a regression line between values of the strain image and values of the first shear wave image in each area of the plural areas; and
   convert the strain image to a second shear wave image of at least one shear wave propagation property based on the regression line.

9. A medium according to claim 8, wherein the program code executable by a computing device to acquire the strain image comprises program code executable by a computing device to:
   acquire the strain image by using forces of acoustic radiation forces or mechanical compression.

10. A medium according to claim 8, wherein the first shear image comprises of at least one image pixel.

11. A medium according to claim 8, wherein the strain image values comprise the strain or the inverse of strain.

12. A medium according to claim 8, wherein the program code executable by a computing device to acquire a shear wave image comprises program code executable by a computing device to:
   apply a first ultrasound pulse to biological tissue to create shear waves in the biological tissue;
   transmit a focused ultrasound pulse into the biological tissue;
   receive one or more ultrasound signals from the biological tissue generated in response to the focused ultrasound pulse;
   detect the shear waves in the biological tissue based on the received one or more ultrasound signals;
   determine at least one shear wave propagation property associated with the detected shear waves; and
   form a first shear wave image of the at least one shear wave propagation property associated with the detected shear waves.

13. A medium according to claim 9, wherein the program code executable by a computing device to acquire the strain image by using the forces comprises program code executable by a computing device to:
   acquire a first ultrasound image before the forces are applied to the biological tissue;
   acquire a second ultrasound image after the forces are applied to the biological tissue;
   calculate tissue displacements between the first and second ultrasound images by a cross correlation, a sum of absolute differences (SAD), a sum of square differences (SSD), a sum of absolute cubic differences (SCD), a sum of absolute power differences (SPD), a color Doppler shift frequency, a color Doppler phase or a color Doppler velocity; and
   calculate the strain image by calculating a spatial derivative of the displacements.

14. A medium according to claim 8, wherein the at least one shear wave propagation property comprises one or more of;
   a propagation velocity associated with one or more of the detected shear waves; and
   a product ($bc^2$) of a real number (b) and the square of the shear wave propagation velocity ($c^2$).

15. A system comprising:
   a memory device;
   a processor to execute computer-executable program code stored in the memory to cause the system to:
   acquire a first shear wave image of at least one shear wave propagation property;
   acquire a strain image;
   divide the strain image and the first shear wave image into plural areas; and
   calculate a regression line between values of the strain image and values of the first shear wave image in each area of the plural areas; and
   convert the strain image to a second shear wave image of at least one shear wave propagation property based on the regression line.

16. A system according to claim 15, wherein acquisition of the strain image comprises acquisition of the strain image by using forces of acoustic radiation forces or mechanical compression.

17. A system according to claim 15, wherein the first shear image comprises at least one image pixel.

18. A system according to claim 15, wherein the strain image values comprise the strain or the inverse of strain.

19. A system according to claim 15, wherein acquisition of a shear wave image comprises:
   application of a first ultrasound pulse to biological tissue to create shear waves in the biological tissue;
   transmission of a focused ultrasound pulse into the biological tissue;
   reception of one or more ultrasound signals from the biological tissue generated in response to the focused ultrasound pulse;
   detection of the shear waves in the biological tissue based on the received one or more ultrasound signals;
   determination of at least one shear wave propagation property associated with the detected shear waves; and
   formation of a first shear wave image of the at least one shear wave propagation property associated with the detected shear waves.

20. A system according to claim 16, wherein acquisition of the strain image by using the forces comprises:
   acquisition of a first ultrasound image before the forces are applied to the biological tissue;
   acquisition of a second ultrasound image after the forces are applied to the biological tissue;
   calculation of tissue displacements between the first and second ultrasound images by a cross correlation, a sum of absolute differences (SAD), a sum of square differences (SSD), a sum of absolute cubic differences (SCD), a sum of absolute power differences (SPD), a color Doppler shift frequency, a color Doppler phase or a color Doppler velocity; and calculation of the strain image by calculating a spatial derivative of the displacements.

21. A system according to claim 15, wherein the at least one shear wave propagation property comprises one or more of;
   a propagation velocity associated with one or more of the detected shear waves; and
   a product ($bc^2$) of a real number (b) and the square of the shear wave propagation velocity ($c^2$).

\* \* \* \* \*